US00PP32385P2

(12) United States Plant Patent
Kerley et al.

(10) Patent No.: US PP32,385 P2
(45) Date of Patent: Oct. 20, 2020

(54) ***PRIMULA* PLANT NAMED 'KERBELBLIC'**

(50) Latin Name: *Primula vulgaris*
Varietal Denomination: KERBELBLIC

(71) Applicants: Timothy Edward Kerley, Cambridge (GB); Sarah Elisabeth Kerley, Cambridge (GB); David William Kerley, Cambridge (GB); Priscilla Grace Kerley, Cambridge (GB)

(72) Inventors: Timothy Edward Kerley, Cambridge (GB); Sarah Elisabeth Kerley, Cambridge (GB); David William Kerley, Cambridge (GB); Priscilla Grace Kerley, Cambridge (GB)

( * ) Notice: Subject to any disclaimer, the term of this patent is extended or adjusted under 35 U.S.C. 154(b) by 0 days.

(21) Appl. No.: 16/602,206

(22) Filed: Aug. 27, 2019

(51) Int. Cl.
*A01H 5/02* (2018.01)
*A01H 6/00* (2018.01)

(52) U.S. Cl.
USPC ..... Plt./472
CPC ..... *A01H 6/00* (2018.05)

(58) Field of Classification Search
USPC ..... Plt./472
CPC ..... A01H 6/00
See application file for complete search history.

(56) References Cited

PUBLICATIONS

UPOV hit on *Primula* plant, 'KERBELBLIC', QZ PBR 20191960, filed Aug. 12, 2019.*

* cited by examiner

*Primary Examiner* — Anne Marie Grunberg
(74) *Attorney, Agent, or Firm* — Cassandra Bright

(57) ABSTRACT

A new and distinct cultivar of *Primula vulgaris* plant named 'KERBELBLIC' is disclosed, characterized by purple and white double flowers, and an abundant, long flowering period. Plants have shown the ability to be propagated by tissue culture at a good rate. Under low temperature and low light conditions, the flowers do not open fully, instead forming a unique rosebud shape. The new variety is a *Primula vulgaris*, suitable for outdoor landscape and container use.

3 Drawing Sheets

Latin name of the genus and species: *Primula vulgaris.*
Variety denomination: 'KERBELBLIC'.

BACKGROUND OF THE INVENTION

The new cultivar is the product of a planned breeding program under the direction of the inventors, David Kerley, Priscilla Kerley, Sarah Kerley, and Timothy Kerley, all citizens of the United Kingdom. The objective of the breeding program was to produce new, compact pot-type *Primula vulgaris* cultivars with abundant double flowers for commercial ornamental purposes. The new cultivar resulted from crossing of two unpatented, unnamed proprietary *Primula vulgaris* seedlings during March of 2010. The selection of the new variety 'Kerbelblic' was made in March 2011, by the inventors at a research greenhouse located in Cambridge, UK.

Asexual reproduction of the new cultivar 'KERBELBLIC' by division was first performed at the same research greenhouse in Cambridge, UK during May of 2011, by division and tissue culture. Both methods have shown that the unique features of this cultivar are stable and reproduced true to type in successive generations. Date of first sale was Aug. 28, 2018. This sale was made directly by the inventor or one who obtained the claimed invention directly or indirectly from the inventor. This sale and all public disclosures made before the filing of this application fall within the exception allowed under 102(b)(1). A CPVO application has been applied for Aug. 12, 2019, having application filing number 20191960.

SUMMARY OF THE INVENTION

The cultivar 'KERBELBLIC' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERBELBLIC' These characteristics in combination distinguish 'KERBELBLIC' as a new and distinct *Primula* cultivar:

1. Purple and white bicolored flowers.
2. Double flowers.
3. Abundant flowering.
4. Long flowering period.
5. Compact and neat plant habit.
6. Good propagation rate in tissue culture.
7. Reliably perennial in many climate zones.
8. Under low temperature and low light conditions, flowers do not open fully, developing a rosebud type appearance.

PARENT COMPARISON

Plants of the new cultivar 'KERBELBLIC' are similar to plants of the seed parent in most horticultural characteristics. However, plants of the new cultivar differ in the following ways:

1. New cultivar has double flowers; seed parent is single flowered.
2. New variety is sterile; seed parent is fertile.
3. New cultivar has a long flowering period; seed parent ceased flowering when seed had set.

Plants of the new cultivar 'KERBELBLIC' are similar to plants of the pollen parent in most horticultural characteristics. However, plants of the new cultivar differ in the following ways:

1. New cultivar has double flowers; pollen parent is single flowered.
2. New variety is sterile; pollen parent is fertile.
3. New cultivar has a long flowering period; pollen parent ceased flowering when seed had set.

COMMERCIAL COMPARISON

Plants of the new variety can be compared to plants of the unpatented *Primula vulgaris* cultivar 'Kerbelil'. In side-by-side comparisons conducted in Over, Cambridge, United Kingdom, plants of the new *Primula* differed from plants of the cultivar 'Kerbelil' in the following characteristics:

1. New variety has purple and white flowers; comparator has purple-violet flowers.
2. This comparator is a slightly taller and wider plant than the new variety.
3. New variety has a dense rosette of petals; this comparator's flower has a looser, more open structure.

Plants of the 'KERBELBLIC' can be compared to plants of the unpatented *Primula vulgaris* cultivar 'Kerbeldawn'. In side-by-side comparisons conducted in Over, Cambridge, United Kingdom, plants of the new *Primula* differed from plants of the cultivar 'Kerbeldawn' in the following characteristics:

1. The new variety is a shorter plant than this comparator.
2. New cultivar is a late season variety; this comparator is a mid-season variety.
3. New variety has purple and white flowers; this comparator has a large yellow spot in the middle of the flower.
4. New variety has a loose, more open flower structure; this comparator has a dense rosette of petals.

BRIEF DESCRIPTION OF THE PHOTOGRAPHS

The accompanying photograph in FIG. 1 illustrates in full color typical plants of 'KERBELBLIC' grown in Over, Cambridge, United Kingdom, in a glass-covered greenhouse and under commercial production practices during the Winter, in low light conditions and low temperature conditions.

Figure 1:
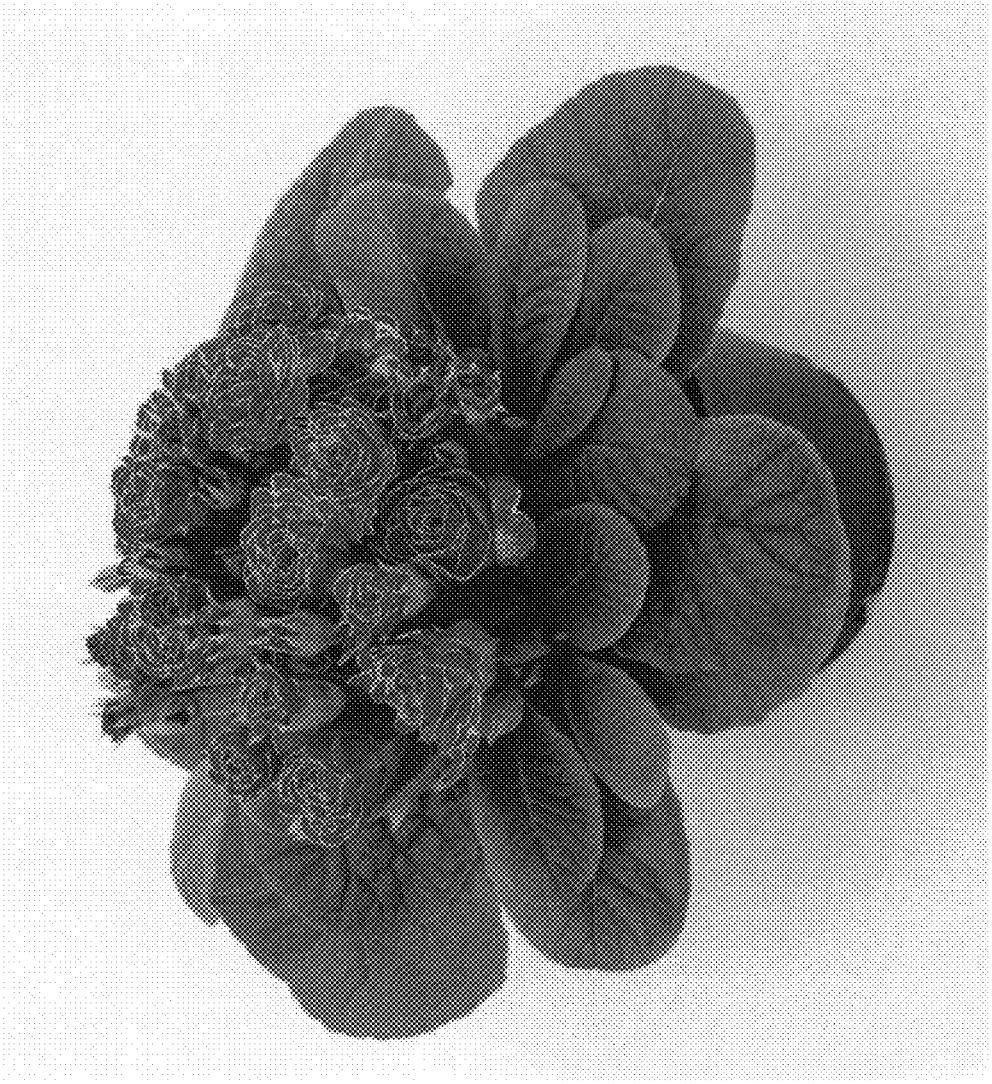
Figure 2:
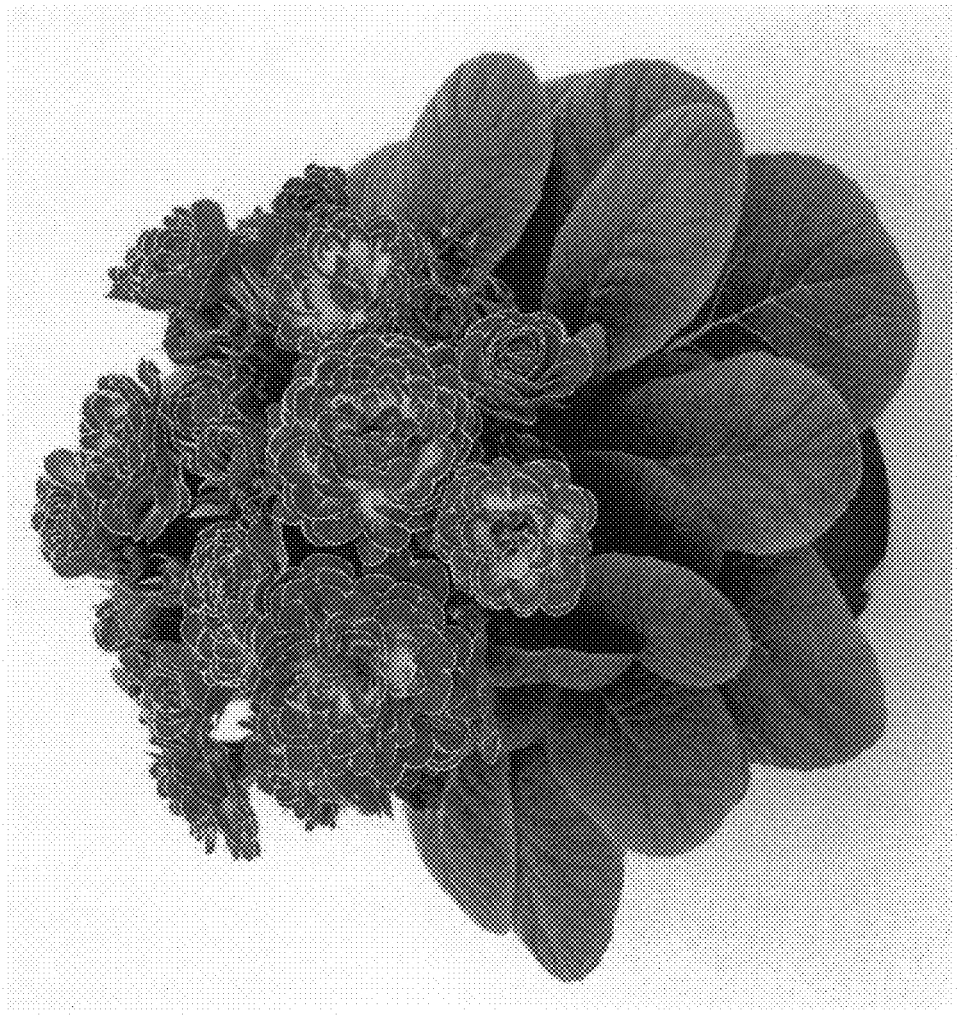
FIG. 2 illustrates a plant of the new variety grown under higher light, higher temperature conditions. Plants in both figures are about five months old when the photographs were taken.
Figure 3:
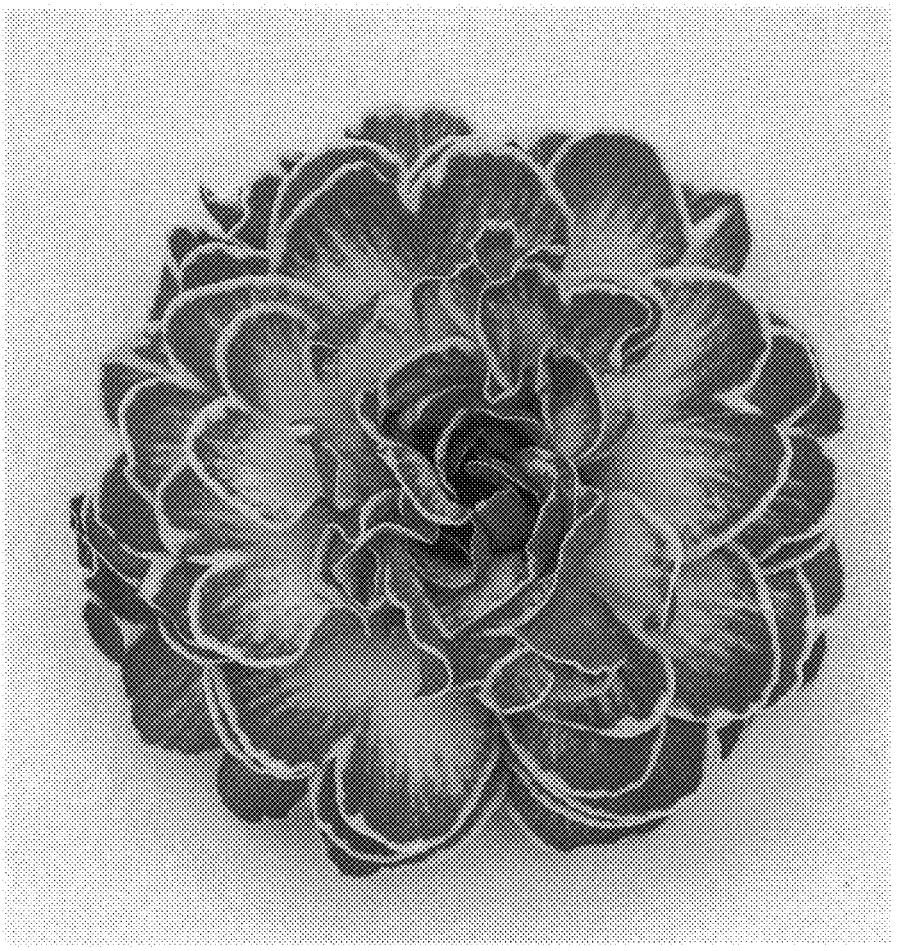
FIG. 3 illustrates a close up of a typical fully opened flower of 'KERBELBLIC', grown under high light, higher temperature conditions.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 1995 except where general terms of ordinary dictionary significance are used. The following observations and measurements describe 'KERBELBLIC' plants grown under commercial production practices during the spring in Cambridge, United Kingdom. During the production of the plants, day temperatures ranged from 5 to 15° C. and night temperatures ranged from 2 to 12° C. No chemical or photoperiodic treatments were given. Measurements and numerical values represent averages of typical flowering types.

Botanical classification: *Primula vulgaris* 'KERBELBLIC'.

Age of the plant described: Approximately 4 to 5 months in an 11 cm pot.

PROPAGATION

Method: Tissue culture.

Time to initiate roots: About 6 weeks at 20° C.

Time to produce a rooted young plant: About six weeks at 20° C.

Root description: Freely branching, fibrous, colored near RHS White 155A.

PLANT

Growth habit: Upright, compact and uniform. Inverted triangle. Vigorous.

Height: Approximately 11 cm.

Plant spread: Approximately 21 cm.

Branching characteristics: No branches, foliage emerges basally.

FOLIAGE

Leaf:

*Arrangement.*—Basal, simple.

*Average length.*—Approximately 10 cm.

*Average width.*—Approximately 4.8 cm.

*Shape of blade.*—Oblanceolate.

*Apex.*—Obtuse.

*Base.*—Acute.

*Margin.*—Slightly undulate, slightly crenate.

*Texture of top surface.*—Smooth, slightly rugose.

*Texture of bottom surface.*—Rugose, hirsute on veins.

*Color.*—Developing foliage upper side: Near RHS Yellow-Green 146A. Developing foliage under side: Near RHS Yellow-Green 146B. Mature foliage upper side: Near RHS Yellow-Green 147A. Mature foliage under side: Near RHS Yellow-Green 146A and 146B.

*Venation.*—Type: Pinnate. Venation color upper side: Between RHS Greyed-Green 193A and B. Venation color under side: RHS Greyed-Green 193A.

Petiole:

*Length.*—1.6 cm.

*Diameter.*—0.5 cm.

*Color.*—Upper Surface: RHS Greyed-Green 193A. Lower Surface: RHS Greyed-Green 193C.

*Texture upper surface.*—Glabrous.

*Texture, lower surface.*—Slightly hirsute.

FLOWER

Bloom period: Recurrent flowering during the Spring under United Kingdom outdoor conditions.

Inflorescence: Solitary, rounded double flowers, upright and outwardly facing.

Persistent or self-cleaning: Persistent.
Fragrance: None.
Flowers and buds per plant: 60-70.
Flower Bud:
*Height.*—2.4 cm.
*Diameter.*—1.7 cm.
*Shape.*—Ovoid.
*Color.*—RHS Purple N78A.
Individual flower:
*Diameter.*—4.8 cm.
*Depth.*—3 cm.
*Petals.*—48-55 per flower, in several concentric whorls.
*Length* (*including tube*).—2.2 to 2.5 cm.
*Width.*—3.1 cm.
*Shape.*—Obcordate.
*Apex.*—Emarginate.
*Margin.*—Entire.
*Texture, upper and lower surfaces.*—Smooth, glabrous.
*Color.*—Developing petals, upper surface: RHS Purple N78A with a thin well-defined rim of White N155B. Lower part of petal N155B, poorly defined margin between N78A and N155B. (Base RHS Yellow 1A not normally visible unless petals are removed from flower). Developing petals, lower surface: Base of petal, RHS White 155A; main color Purple N78D deepening to N78A at outer edge. Mature petals, upper surface: RHS Purple N78A, flushed Red-Purple N74A, with a thin defined rim of White N155B/C. Lower half of petal N155B, poorly defined margin. (Base RHS Yellow 1A not normally visible unless petals are removed from flower). Mature petals, Lower surface: RHS Purple N78B, N78A at outer edge with very fine rim of White N155B. Small blotch of N155B at petal base.
*Sepals.*—Quantity per flower: 6-7 in a single whorl; fused at base. Length: 2.3 cm. Width: 0.6 cm. Shape: Lanceolate. Apex: Acute. Texture, upper surface: Smooth, glabrous. Texture, lower surface: Glabrous, hirsute along central vein. Color, upper surface: RHS Yellow-Green 146D. Color, lower surface: RHS Yellow-Green 146C.
Peduncle:
*Length.*—8.7 cm.
*Diameter.*—0.2 cm.
*Orientation.*—Erect.
*Strength.*—Strong.
*Color.*—RHS Greyed-Green 195B with a flush of Grey-Brown 199B/C.
*Texture.*—Pubescent.

REPRODUCTIVE ORGANS

Development of reproductive organs has not been observed.

OTHER CHARACTERISTICS

Disease resistance: Plants of the new *Primula* have not been noted to be resistant to pathogens and pests common to *Primula*.
Temperature tolerance: Plants of the new *Primula* have been observed to have tolerated temperatures from about −5 to 28° C.
Fruit/seed production: Fruit and seed production not observed, flowers are sterile.

What is claimed is:

1. A new and distinct cultivar of *Primula* plant named 'KERBELBLIC' as herein illustrated and described.

* * * * *